US00PP35130P2

(12) United States Plant Patent
Vandenberg

(10) Patent No.: US PP35,130 P2
(45) Date of Patent: Apr. 25, 2023

(54) ***HIBISCUS* PLANT NAMED 'WHITE TREASURE WIND'**

(50) Latin Name: *Hibiscus rosa-sinensis*
Varietal Denomination: White Treasure Wind

(71) Applicant: Cornelis P. Vandenberg, Fort Myers, FL (US)

(72) Inventor: Cornelis P. Vandenberg, Fort Myers, FL (US)

(73) Assignee: ARIS HORTICULTURE, INC., Barberton, OH (US)

( * ) Notice: Subject to any disclaimer, the term of this patent is extended or adjusted under 35 U.S.C. 154(b) by 0 days.

(21) Appl. No.: 17/863,380

(22) Filed: Jul. 12, 2022

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

(56) References Cited

U.S. PATENT DOCUMENTS

PP18,998 P3 * 7/2008 Smith ..... A01H 6/608 Plt./257

* cited by examiner

*Primary Examiner* — Susan McCormick Ewoldt
(74) *Attorney, Agent, or Firm* — C. Anne Whealy

(57) ABSTRACT

A new and distinct cultivar of *Hibiscus* plant named 'White Treasure Wind', characterized by its semi-upright and uniformly mounded plant habit appropriate for container production; freely branching habit, dense and bushy appearance; glossy dark green-colored leaves; uniform, freely and early flowering habit; single white-colored flowers with dark red-colored centers; good postproduction and garden performance; and tolerance to Bacterial Leaf Spot.

2 Drawing Sheets

Figure 1:
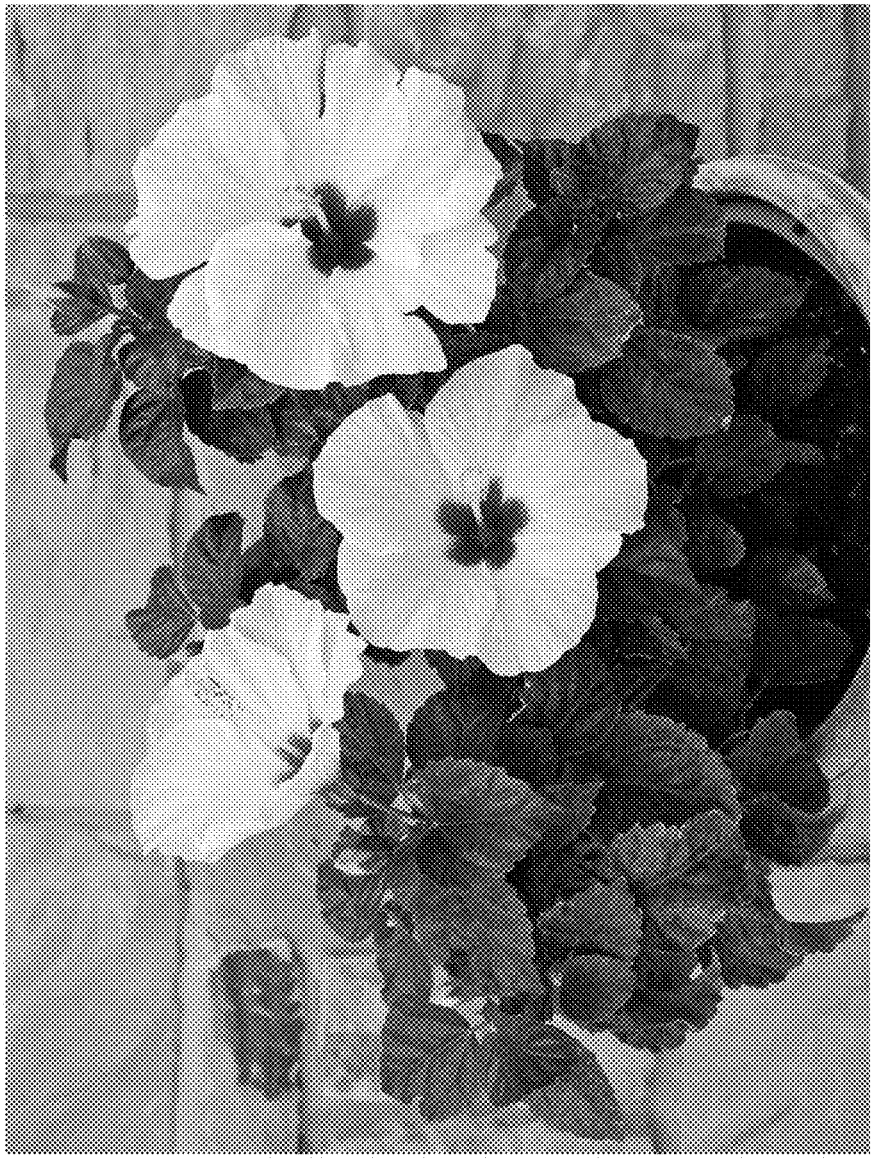

Botanical designation: *Hibiscus rosa-sinensis.*
Cultivar denomination: 'WHITE TREASURE WIND'.

BACKGROUND OF THE INVENTION

The present invention relates to a new and distinct *Hibiscus* plant, botanically known as *Hibiscus rosa-sinensis* and hereinafter referred to by the name 'White Treasure Wind'.

The new *Hibiscus* plant is a product of a planned breeding program conducted by the Inventor in Alva, Fla. The objective of the breeding program is to create new freely-branching *Hibiscus* plants with uniform plant habit appropriate for container production, early and freely flowering habit, desirable flower color, good garden performance and resistance to Bacterial Leaf Spot.

The new *Hibiscus* plant originated from a cross-pollination made by the Inventor in Alva, Fla. in 2014 of *Hibiscus rosa-sinensis* 'Luau Pink Paki', not patented, as the female, or seed, parent with *Hibiscus rosa-sinensis* 'Caribbean Pink', not patented, as the male, or pollen, parent. The new *Hibiscus* plant was discovered and selected by the Inventor as a single flowering plant within the progeny of the stated cross-pollination in a controlled greenhouse environment in Alva, Fla. on Aug. 11, 2015.

Asexual reproduction of the new *Hibiscus* plant by vegetative terminal cuttings in a controlled greenhouse environment in Alva, Fla. since November, 2015 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'White Treasure Wind'. These characteristics in combination distinguish 'White Treasure Wind' as a new and distinct *Hibiscus* plant:

1. Semi-upright and uniformly mounded plant habit appropriate for container production.
2. Freely branching habit, dense and bushy appearance.
3. Glossy dark green-colored leaves.
4. Uniform, freely and early flowering habit.
5. Single white-colored flowers with dark red-colored centers.
6. Good postproduction and garden performance.
7. Tolerance to Bacterial Leaf Spot.

Plants of the new *Hibiscus* can be compared to plants of the female parent, 'Luau Pink Paki'. Plants of the new *Hibiscus* differ primarily from plants of 'Luau Pink Paki' in the following characteristics:

1. Plants of the new *Hibiscus* are more uniform in plant habit than plants of 'Luau Pink Paki'.
2. Plants of the new *Hibiscus* are more uniform in flowering habit than plants of 'Luau Pink Paki'.
3. Flowers of plants of the new *Hibiscus* are white in color whereas flowers of plants of 'Luau Pink Paki' are light pink in color.
4. Flowers of plants of the new *Hibiscus* last about two to three days whereas flowers of plants of 'Luau Pink Paki' last about one day.

Plants of the new *Hibiscus* can be compared to plants of the male parent, 'Caribbean Pink'. Plants of the new *Hibiscus* differ primarily from plants of Caribbean Pink' in the following characteristics:

1. Plants of the new *Hibiscus* are more vigorous than plants of 'Caribbean Pink'.
2. Plants of the new *Hibiscus* are more freely flowering than plants of 'Caribbean Pink'.
3. Flowers of plants of the new *Hibiscus* are white in color whereas flowers of plants of 'Caribbean Pink' are pink in color.
4. Flowers of plants of the new *Hibiscus* last about two to three days whereas flowers of plants of 'Caribbean Pink' last about one day.

Plants of the new *Hibiscus* can be compared to plants of the *Hibiscus rosa-sinensis* 'Ivory Wind', disclosed in U.S. Plant Pat. No. 31,353. In side-by-side comparisons plants of the new *Hibiscus* differ from plants of 'Ivory Wind' in the following characteristics:

1. Plants of the new *Hibiscus* are more vigorous than plants of 'Ivory Wind'.
2. Flowers of plants of the new *Hibiscus* are larger and whiter in color than flowers of plants of 'Ivory Wind'.
3. Flowers of plants of the new *Hibiscus* last about two to three days whereas flowers of plants of 'Ivory Wind' last about one day.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet (FIG. 1) is a side perspective view of typical flowering plants of 'White Treasure Wind' grown in a container.

Figure 2:
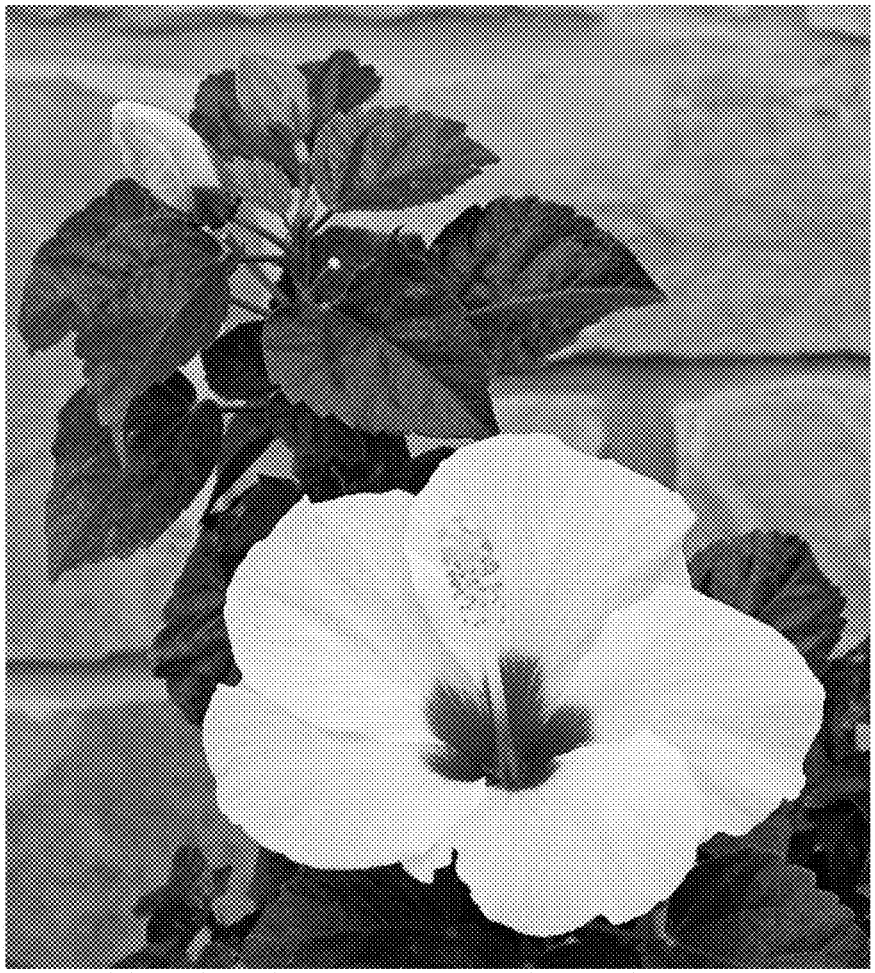

The photograph on the second sheet (FIG. 2) is a close-up view of a typical flowering plant of 'White Treasure Wind' showing developing flower buds and a fully developed flower.

DETAILED BOTANICAL DESCRIPTION

The aforementioned photographs and following observations, measurements and values describe plants grown during the summer in 15-cm containers in a polyethylene-covered greenhouse in Alva, Fla. and in 24-cm containers in an outdoor nursery in Fort Worth, Tex. under cultural practices which closely approximate commercial *Hibiscus* production. During the production of the plants in Texas, day temperatures ranged from 35° C. to 40° C., night temperatures ranged from 24° C. to 35° C. and light levels ranged from 5,000 to 7,500 foot-candles. Plants were pinched two times and were nine months old when the photographs and the description were taken. In the description, color references are made to The Royal Horticultural Society Colour Chart, 2015 Edition, except where general terms of ordinary dictionary significance are used.

Botanical classification: *Hibiscus rosa-sinensis* 'White Treasure Wind'.

Parentage:

*Female, or seed, parent.*—*Hibiscus rosa-sinensis* 'Luau Pink Paki', not patented.

*Male or pollen parent.*—*Hibiscus rosa-sinensis* 'Caribbean Pink', not patented.

Propagation:

*Type.*—By vegetative terminal cuttings.

*Time to initiate roots, summer and winter.*—About four to five weeks.

*Time to produce a rooted young plant, summer and winter.*—About five to six weeks.

*Root description.*—Thick, fibrous; typically white to light brown in color, actual color of the roots is dependent on substrate composition, water quality, fertilizer, substrate temperature and physiological age of roots.

*Rooting habit.*—Moderate branching; moderately dense.

Plant description:

*Plant form and growth habit.*—Perennial, evergreen, semi-upright and uniformly mounded plant habit; moderately vigorous to vigorous growth habit.

*Branching habit.*—Freely branching habit with lateral branches potentially develop at every node; pinching enhances lateral branch development; dense and bushy appearance.

*Plant height.*—About 39 cm.

*Plant diameter* (*area of spread*).—About 48 cm.

Lateral branch description:

*Length.*—About 28 cm.

*Diameter.*—About 5 mm.

*Internode length.*—About 1.8 cm to 2.4 cm.

*Aspect.*—Upright to somewhat outwardly spreading.

*Texture and luster, immature.*—Smooth; glossy.

*Texture and luster, mature.*—Woody and slightly rough; matte.

*Color, immature.*—Close to 144A.

*Color, mature.*—Close to 199A and 199B.

Leaf description:

*Arrangement.*—Alternate, single; numerous; symmetrical.

*Length.*—About 7.2 cm to 7.4 cm.

*Width.*—About 6.3 cm to 6.7 cm.

*Shape.*—Broadly ovate with cordate tendencies.

*Apex.*—Acute.

*Base.*—Cordate.

*Margin.*—Crenate.

*Texture and luster, upper surface.*—Smooth, glabrous; glossy.

*Texture and luster, lower surface.*—Smooth, glabrous; semi-glossy.

*Venation pattern.*—Pinnate; arcuate.

*Color.*—Developing leaves, upper surface: More green than NN137A. Developing leaves, lower surface: Close to between 147A and 146A. Fully expanded leaves, upper surface: Close to between 147A and 139A; venation, close to 147A. Fully expanded leaves, lower surface: Close to between 147A and 146A; venation, close to 146A to 146B.

*Petioles.*—Length: About 2.1 cm to 2.4 cm. Diameter: About 3 mm. Texture and luster, upper and lower surfaces: Smooth, glabrous; semi-glossy. Color, upper surface: Close to 146A. Color, lower surface: Close to 144A.

Flower description:

*Flower arrangement and flowering habit.*—Rounded single flowers arranged at terminal leaf axils; uniform and freely flowering habit with about three or five flowers per terminal; flowers face mostly upright to slightly outwardly.

*Natural flowering season.*—Plants of the new *Hibiscus* flower naturally during the spring and summer or during periods of warm weather; plants flower year-round in the greenhouse.

*Flower longevity.*—Depending on temperature and water status, flowers typically last about two to three days on the plant; flowers persistent.

*Flower diameter.*—About 10.75 cm.

*Flower length* (*height*).—About 7.5 cm.

*Flower buds.*—Resistance to abscission during shipping: Plants of the new *Hibiscus* have been observed to resist flower bud drop during shipping. Length: About 1.8 cm. Diameter: About 1 cm. Shape: Ovoid. Texture and luster: Smooth, glabrous; slightly glossy. Color: Close to 146A.

*Petals.*—Arrangement: Corolla consists of a single whorl of five petals that are fused at base; petals imbricate. Length: About 7.1 cm. Width: About 6.1 cm. Shape: Broadly spatulate. Apex: Rounded. Base: Attenuate. Margin: Entire; slightly undulate. Texture and luster, upper surface: Smooth, glabrous; slightly glossy and towards the base, glossy. Texture and luster, lower surface: Glabrous; veins prominent; semi-glossy. Color: When opening and fully opened, upper surface: Close to 157C; towards the base, close to 53A; venation, similar to lamina colors, close to 157C and 53A. When opening and fully opened, lower surface: Close to 157A and 157B; venation, similar to lamina colors, close to 157A and 157B.

*Sepals.*—Appearance: Five sepals in a single whorl fused into a tubular star-shaped calyx. Length: About 2.75 cm. Width: About 1.2 cm. Shape: Lanceolate. Apex: Sharply acute. Margin: Entire. Texture and luster, upper surface: Smooth, glabrous; waxy; glossy. Texture and luster, lower surface: Smooth, glabrous; slightly glossy. Color, upper surface: Close to 146C. Color, lower surface: Close to 146A to 146B.

*Epicalyx.*—Quantity and arrangement: About seven in a single whorl fused at base. Length: About 1.1 cm. Width: About 4 mm. Shape: Narrowly lanceolate. Apex: Sharply acute. Margin: Entire. Texture and luster, upper and lower surfaces: Smooth, glabrous; slightly glossy. Color, upper and lower surfaces: Close to 147A.

*Peduncles.*—Length: About 2.75 cm. Diameter: About 2.5 mm. Aspect: Upright to slightly outward. Strength: Strong, flexible. Texture and luster: Smooth, glabrous; slightly glossy. Color: Close to 144A.

*Reproductive organs.*—Androecium: Stamen number: Numerous, about 55 to 65 per flower. Filament length: About 3 mm. Filament color: Close to 157C. Anther shape: Oblong. Anther length: About 1.5 mm. Anther color: Close to 14A. Amount of pollen: If present, scarce. Pollen color: Close to 14A. Gynoecium: Pistil number: One per flower. Pistil length: About 6.75 cm. Style length: About 5.8 cm. Style texture and luster: Smooth, glabrous; waxy; semi-glossy. Style color: Close to 157A to 157B. Stigma appearance: Five-parted, rounded. Stigma color: Close to 6A. Ovary color: Close to between 154D and 11D.

*Seeds and fruits.*—To date, seed and fruit production has not been observed on plants of the new *Hibiscus*.

Garden performance: Plants of the new *Hibiscus* have been observed to have good garden performance and to tolerate wind, rain and temperatures ranging from about 1° C. to about 40° C.

Pathogen & pest resistance: Plants of the new *Hibiscus* have been observed to be tolerant to Bacterial Leaf Spot (*Pseudomonas cichorii*). To date, plants of the new *Hibiscus* grown under Florida production conditions have not been shown to be resistant to pests and other pathogens common to *Hibiscus* plants.

It is claimed:

1. A new and distinct *Hibiscus* plant named 'White Treasure Wind' as illustrated and described.

* * * * *